United States Patent
Toole et al.

(10) Patent No.: US 10,611,437 B2
(45) Date of Patent: Apr. 7, 2020

(54) ARTICULATING MOORED PROFILER SYSTEM

(71) Applicants: WOODS HOLE OCEANOGRAPHIC INSTITUTION, Woods Hole, MA (US); John M. Toole, Woods Hole, MA (US); Kenneth W. Doherty, Woods Hole, MA (US); Jeffrey K. O'Brien, Woods Hole, MA (US); Frederik T. Thwaites, Woods Hole, MA (US)

(72) Inventors: John M. Toole, Woods Hole, MA (US); Kenneth W. Doherty, Woods Hole, MA (US); Jeffrey K. O'Brien, Woods Hole, MA (US); Frederik T. Thwaites, Woods Hole, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 88 days.

(21) Appl. No.: 15/762,395

(22) PCT Filed: Oct. 3, 2016

(86) PCT No.: PCT/US2016/055159
§ 371 (c)(1),
(2) Date: Mar. 22, 2018

(87) PCT Pub. No.: WO2017/059423
PCT Pub. Date: Apr. 6, 2017

(65) Prior Publication Data
US 2018/0297669 A1     Oct. 18, 2018

Related U.S. Application Data

(60) Provisional application No. 62/236,288, filed on Oct. 2, 2015.

(51) Int. Cl.
*G01C 13/00* (2006.01)
*B63B 22/00* (2006.01)
(Continued)

(52) U.S. Cl.
CPC ............. *B63B 22/18* (2013.01); *B63B 1/34* (2013.01); *G01C 13/00* (2013.01); *G01C 13/004* (2013.01);
(Continued)

(58) Field of Classification Search
CPC ...... G01N 33/1886; G01N 33/18; G01N 1/12; G01N 2001/021; G01N 1/10; G01N 1/16;
(Continued)

(56) References Cited

U.S. PATENT DOCUMENTS 3,383,915 A * 5/1968 Gilbert ............... G01C 13/006
73/170.31
4,157,657 A * 6/1979 Hinchman ......... G01N 33/1886
254/333

(Continued)

FOREIGN PATENT DOCUMENTS

EP     1031855 A2     8/2000

OTHER PUBLICATIONS

"A Moored Profiling Instrument" (Doherty et al.) Journal of Atmospheric and Oceanic Technology, vol. 16, Dec. 3, 1998 (Dec. 3, 1998) entire document, especially Title, Abstract, fig. 1; p. 1818, in 1-17, p. 1819-1821.
(Continued)

*Primary Examiner* — Andre J Allen
(74) *Attorney, Agent, or Firm* — Robert Devin Ricci; Russel O. Primeaux; Kean Miller LLP

(57) ABSTRACT

The present invention relates to profiler systems and methods for observing and sensing aspects of a body of water at a plurality of depths. A water profiler is disclosed compris-
(Continued)

ing, generally, a vessel body connected to an external mooring cable via an attachment means, a drive means for maneuvering the vessel body longitudinally about the mooring cable; an articulating mechanism; and a sensor array capable of measuring a parameter for study wherein the vessel body is capable of articulating about the mooring cable. In alternate embodiments, the articulation allows the vessel body to be placed in relation with the three dimensional current such that at least one sensor is positioned into the current so as to sample or measure undisturbed water. In alternate embodiments, hydrofoils or wings are mounted to the vessel body that can be manipulated to harness the current force and maneuver the vessel body.

29 Claims, 13 Drawing Sheets

(51) Int. Cl.
  *B63B 23/18* (2006.01)
  *B63B 22/18* (2006.01)
  *G01N 33/18* (2006.01)
  *B63B 1/34* (2006.01)
  *G01C 15/00* (2006.01)

(52) U.S. Cl.
  CPC ....... *G01C 13/006* (2013.01); *G01N 33/1886* (2013.01); *B63B 2211/02* (2013.01); *G01C 15/00* (2013.01); *G01N 33/18* (2013.01)

(58) Field of Classification Search
  CPC ............... G01N 33/1806; G01N 1/14; G01N 2021/6432; G01N 2021/6434; G01N 21/763; G01N 21/78; G01N 21/80; G01N 33/1826; G01N 33/24; G01N 3/42; G01N 15/04; G01N 17/008; G01N 1/04; G01N 1/18; G01N 1/2035; G01N 1/22; G01N 2015/0088; G01N 2021/1772; G01N 2021/1793; G01N 2021/4769; G01N 2021/556; G01N 2033/1873; G01N 2035/00881; G01N 21/15; G01N 21/55; G01N 2203/0082; G01N 2203/0682; G01N 33/246; G01N 3/064; G01N 3/34; G01N 7/14; G01C 13/00; G01C 13/008; G01C 13/002; G01C 13/004; G01C 13/006; G01C 5/06
  USPC .......................................... 73/170.29–170.34
  See application file for complete search history.

(56) References Cited

U.S. PATENT DOCUMENTS

| | | | | | |
|---|---|---|---|---|---|
| 4,543,014 | A | * | 9/1985 | Brandi | B63B 22/021 |
| | | | | | 114/230.13 |
| 4,924,698 | A | * | 5/1990 | Echert | B63B 22/18 |
| | | | | | 441/33 |
| 5,869,756 | A | * | 2/1999 | Doherty | B63B 22/18 |
| | | | | | 405/188 |
| 2008/0277492 | A1 | * | 11/2008 | Cannon | A01G 15/00 |
| | | | | | 239/14.1 |
| 2010/0246331 | A1 | * | 9/2010 | Paul | F16L 11/086 |
| | | | | | 367/173 |

OTHER PUBLICATIONS

"Moored Profiler"—Ocean Instruments (WHOI.edu) Apr. 7, 2014 (Apr. 7, 2014) [online], <URL:https://web.archive.org/web/20140404224721/http://www.whoi.edu/instruments/viewinstrument.do?id=10978>entire document.

* cited by examiner

ARTICULATING MOORED PROFILER SYSTEM

CROSS REFERENCE TO RELATED APPLICATIONS

This application is the National Stage of International Application No. PCT/US2016/55159, filed Oct. 3, 2016, which claims the benefit of U.S. Patent Application Ser. No. 62/236,288, filed Oct. 2, 2015. Furthermore, the entire contents of the U.S. Pat. No. 5,869,756 "Moored Water Profiling Apparatus" filed Feb. 11, 1007 and U.S. Pat. No. 5,665,909 "Free-Fall, Wire Guided Hydrographic Profiler" filed May 17, 1996 are incorporated herein by reference and without disclaimer.

FIELD OF THE INVENTION

The present invention generally relates to techniques for observing and conducting experiments on aspects of a water column, particularly in deep water and strong water currents over a period of time using one or more sensors and/or samplers.

BACKGROUND OF THE INVENTION

Measurements of physical and chemical attributes of water bodies are commonly made by lowering instruments from a surface vessel to the bottom of a body of water such as the ocean, a lake, or a river. Water depths can range from a few meters to nearly ten thousand meters. The location from which the data is taken is commonly referred to as a hydrographic station. The water properties can change substantially over time. Therefore, the frequency of measurement needs to be commensurate with the rate of change of the water properties.

The frequency by which these measurements can be made is governed by the logistics of re-occupying the observation locations or stations. It is now recognized that a number of important ocean circulation and limnological phenomena occur episodically, and that there are short and long-term changes in water properties. More frequent sampling, or sampling initiated by a measured change in the environment, is needed to elucidate ocean or lake behavior.

While such frequent measurements have been extremely difficult to obtain, the limited number of studies that have re-occupied the same site many times over a period have proven to be extremely valuable. For example, an investigation by J. R. Lazier in 1980 of the Labrador Sea documented the effect of low-salinity surface water on deep water convection. Undoubtedly, many other important discoveries concerning ocean water circulation await the ability to obtain long-term profiles of water properties. There remain to date scientific and operational needs for sustained ocean observations at fixed locations. Despite advances in drifting, gliding, and self-propelled autonomous instruments, use of these technologies to form "virtual moorings" over long time periods are only practical in modest ocean current environments. Long-term measurements at fixed locations are traditionally made using moored instrument systems. At a limited number of preselected depths, an instrument package is affixed to the mooring cable which is anchored to the sea floor. Traditional moored profilers are deployed on a bottom-anchored mooring; therefore, they generally remain on station even in strong flows, but their functionality is limited. For example, while the traditional profiler may be preferable to single observations, the profile over time is severely constrained by a limited number of sampling depths. Maintaining calibration of many instrument packages is time-consuming and expensive. Since each preselected depth requires its own complete instrument package, the cost to obtain the data increases proportionately to the number of sites selected.

It has been recognized that a single sensor platform that can move up and down the mooring cable may provide distinct advantages by eliminating the need for multiple sensors and multiple tethering systems. It may also provide the advantages of a single calibration applicable to all of the measurements. This is particularly important in long-term measurements where sensor drift over time may be large compared to the ocean variability.

Previous moored profiler models have been in use for the past two decades to address the need or desire to observe water properties and currents at fixed geographic locations. These profilers are traditionally propelled vertically on a mooring cable using a traction drive wheel. While these models have returned unique and valuable observations, such models have also suffered from endurance issues (often less than 1,000 km of profiling per deployment). This endurance problem is particularly problematic as profilers are routinely meant to be disposed in the water column for time periods of a year or longer. Additionally, these profilers lack the ability to provide reliable track records for profiling. It would be desirable for a profiler to fully span its programmed sampling depth range especially during times of strong incident ocean currents. Likewise, traditional profilers have suffered great issues with reliability with regards to data collection and retention. A frustrating number of mooring profiler deployments have returned incomplete profiles and/or sampled for less than planned periods due to issues such as premature battery depletion. Given the number of variables at play in an ocean environment, a failed or only partially successful deployment means, from a scientific standpoint, the complete loss of information that will likely never be acquired or duplicated. These performance issues have dampened community interest in using and inventing in profilers.

Existing moored systems also suffer from a number of other functional defects. For example, they routinely fail to reach bottom stop depth while having limits on depth of operation. Others slip by losing traction of the drive wheel. Still others have suffered from lost performance in strong water currents. As a whole, the units have been unreliable at times, either concerning the ability to stay at specific depth when resting between profiles or inconsistent profiling speeds or unreliable time series and data collection which causes profiles to exceed allotted amounts of batter power.

Therefore, there is an unmet need for a re-designed mooring profiler able to better support oceanographic research and industrial programs that, in one or more embodiments, is adapted for use in strong current conditions with increased reliability and length of deployment in addition to a higher quality data return. A redesigned Articulating Moored Profiler System is provided herein which, in one or more embodiments, seeks to provide at least one of the following benefits: (1) improved profiling reliability across various environments, including stronger flows and in instances of misballasting; (2) increased profiler endurance; (3) a more flexible layout in relation to where sensors can be mounted onto or inserted into the profiling vehicle which may include the ability to place sensors outside the fluid boundary layer of the vehicle; (4) a streamline sensor interface which can improve the operator interface and/or enhance the flexibility of data logging; and (5) a more robust and better quality brake system.

DESCRIPTION OF THE DRAWINGS

The drawings constitute a part of this specification and include exemplary embodiments of the Articulating Moored Profiler (AMP) System, which may be embodied in various forms. It is to be understood that in some instances, various aspects of the invention may be shown exaggerated or enlarged to facilitate an understanding of the invention. It should be understood that the drawings are not necessarily to scale; instead, emphasis has been placed upon illustrating the principles of the invention. In addition, in the embodiments depicted herein, like reference numerals in the various drawings refer to identical or near identical structural elements. Other features and advantages of the present invention, as well as the invention itself, can be more fully understood from the following description of the various embodiments, when read together with the accompanying drawings, in which:

FIG. 6 is a schematic view of the embodiment from FIG. 4 to show the components of the embodiment wherein

FIG. 8 shows various angles of the attachment means used in one embodiment of the articulating moored profiler to attach the vessel body to the mooring wire. As shown, FIG. 8A is a straight on view of the attachment means while

FIG. 11 depicts flow modeling over the system fin design shown in terms of water velocity vectors. As shown.

SUMMARY OF THE INVENTION

Figure 1:
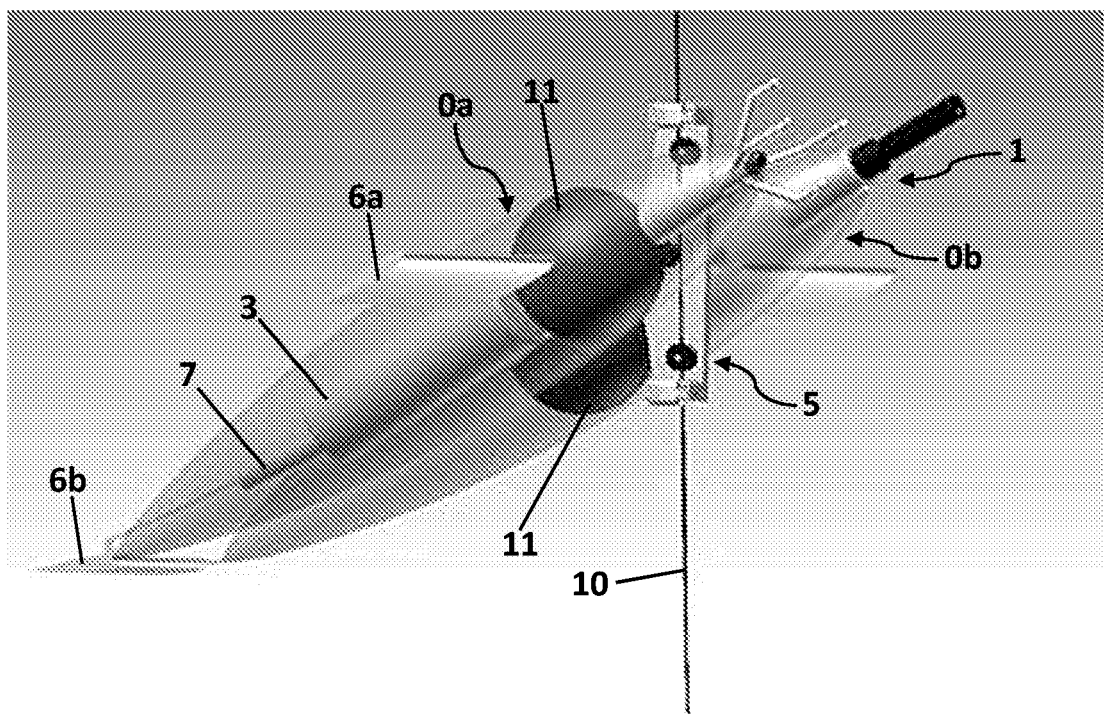
FIG. 1 depicts a side view of one illustrated embodiment of the articulated moored profiler moving about a mooring wire in a strong ocean current. In this embodiment, two slim, streamlined bodies are arrayed on either side of the propulsion core (drive motor and guide sheaves mounted in a dedicated structure) with the Conductivity/Temperature/Depth (CTD) sensor in one body and a modified modular acoustic velocity sensor (MAVS)/acoustic current meter (ACM) in the other. The MAVS transducer arrangement is optimized to sense flow directed into the sensor. An adjustable tail fin orients the body relative to the incident three-dimensional relative flow such that the wings derive lift from the ocean current past the mooring.

The present invention relates to systems and methods for a water profiling device designed for streamlined operation in the strong water currents of an aquatic environment such as the ocean, a lake, a river, among others, to provide high reliability and longer endurance during deployment in addition to increased sampling capabilities using a high resolution sensor array.

A water profiler is disclosed and claimed herein comprising, generally,
  a. a vessel body connected to an external mooring cable via an attachment means,
  b. a drive means for maneuvering the vessel body longitudinally about the mooring cable;
  c. an articulating mechanism; and
  d. a sensor array capable of measuring a parameter for study.

In one or more embodiments, at least one sensor of the sensor array is disposed within the body. In alternate embodiments, the sensor array is capable of measuring at least one parameter selected from the group comprising conductivity, temperature, depth, turbidity, dissolved gas, fluorescence, pressure, light level, pH, a chemical, electrical current, battery status, and water current velocity.

In alternate embodiments, the vessel body is capable of articulating about the mooring cable via the articulating mechanism. In a preferred embodiment, the vessel body is capable of articularing about the mooring cable so as to place the vessel body in relation with the three dimensional current. In alternate embodiments, the vessel body is articulated such that at least one sensor is positioned into the current so as to sample or measure undisturbed water.

In one or more embodiments, hydrofoils or wings are mounted to the vessel body to assist with the hydrodynamics of the vessel body. In alternate embodiments, the wings can be manipulated to harness the current force and maneuver the vessel body.

In embodiments wherein the profiler is used at too great of a depth to draw power from the surface, an onboard power source such as a battery is employed.

DETAILED DESCRIPTION OF THE ILLUSTRATED EMBODIMENTS

The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

Furthermore, the described features, structures, or characteristics may be combined in any suitable manner in one or more embodiments. In the following description, numerous specific details are provided, such as examples of vessels, water jets, deploying means, and sensors. One skilled in the relevant art will recognize, however, that the Articulating Moored Profiler System may be practiced without one or more of the specific details, or with other methods, components, materials, and so forth. In other instances, well-known structures, materials, or operations are not shown or described in detail to avoid obscuring aspects of the invention. Other components and apparatuses may be conceived that are equivalent in function, logic, or effect to one or more mechanisms, or portions thereof, of the illustrated Articulating Moored Profiler ("AMP") System.

The invention may be better understood through the following detailed description describing various embodiments to a system adapted to repeatedly transport a sensor suite vertically through the water column to acquire high vertical and high temporal resolution observations of various aspects and parameters of the sampled body of water.

Scientific and operational needs exist for sustained ocean observations at fixed geographic locations. Despite advances in drifting, gliding, and self-propelled autonomous instruments, existing technologies used to form "vertical moorings" have yet to fill the void for long-term deployments in conditions more than modest ocean currents (e.g., 25 cm/s or less). Other mooring profilers, deployed on bottom-anchored moorings, are capable of remaining on station in strong water flows (e.g., 25 cm/s or greater, up to 1 m/s, 2 m/s, 3 m/s) but lose functionality, reliability, and/or accuracy of measurements. Existing moored profilers suffer additional drawbacks including the fact that that the sensor integration into the profilers is restrictive (both electronically and physically), preventing further adaption to the needs of the user.

An improved articulated moored profiler device is described and claimed herein that is (1) capable of supporting a plurality of ocean science studies currently desired in the field, including the response of ocean flows incident on bathymetric features, and (2) is adaptable to meet the needs of future research. The AMP device is designed to address the shortcomings of existing models while further enhancing the profiler device's capabilities. In so doing, numerous advancements have been incorporated into the AMP that relate to the profiling vehicle itself and its interface with a variety of sensors. Additionally, in various embodiments, the AMP device incorporates one or more of the following advantages over the prior art: improved profiling reliability, particularly in stronger flows and in cases of misballasting, increased profiling endurance, more flexibility in where sensors may be effectively mounted on the profiling vehicle and collection of higher resolution sensor data by placing them (or a sensor inlet) outside the fluid boundary layer of the vehicle, streamlined sensor interfacing, improved operator interface, enhanced flexibility of logging and collecting additional and more thorough diagnostics of system performance, and implementation of a higher quality functioning braking system. Furthermore, the AMP device manages these advancements while continuing to be reasonable in size and weight to manage on the deck of a vessel or platform during deployment and at recovery.

The AMP device disclosed herein comprises, generally, a longitudinal vessel body 0, a sensor array comprising one or more sensors 1, a drive motor assembly 2, an electronics housing 3, a controller 4, an attachment mechanism 5 for connecting the vessel body 0 to a mooring wire (i.e., an external cord or cable) 10, a lift assist system 6, a lift control system 7, an articulating mechanism 8, and at least one power source 9 in electronic communication with the sensor array 1, controller 4, lift control system 7 and/or articulating mechanism 8.

The overall design provides a longitudinal vessel body 0 that is able to articulate (e.g., pivot, maneuver, align) about the mooring wire 10 through an articulating mechanism 8 to align the vessel body 0 with the relative three-dimensional incident flow. As depicted, the longitudinal vessel body 0 comprises a relatively long, thin cylindrical body that extends from a front or bow section (also referred to as the "leading end" when discussing orientation into the current flow) to an aft section with a middle or belly section in between the front and aft sections. The overall length and girth of the vessel body are a balancing act to increase storage capacity for sensors, electrical equipment, and power supplies (i.e., batteries), while reducing the drag that current will have on the vessel body. This balancing in engineering must further incorporate the buoyancy of the system, particularly as the system articulates and pivots about the mooring wire (e.g., cable). As will be discussed, various embodiments of the AMP have the capability to employ several means for adjusting buoyancy before and during operations such as the buoyancy spheres 11.

The attachment means 5 secures the vessel body 0 to the mooring wire 10 in such a manner to allow the vessel body 0 to efficiently pivot/swivel into the present current flow while resisting the water forces from unintentionally altering the system profiling. As depicted, the attachment means 5 is connected to the longitudinal vessel body 0 forward of the middle section; however, it is possible for the attachment means to be connected at either the most front, middle, or most aft ends as well. Because the attachment means 5 as depicted is connected to the longitudinal vessel body 0 at a position forward of the middle section, the terms leading end (e.g., front section), middle section, or tail end (e.g., aft section) are relative as they can be interchanged depending on the configurations. The distinctions are purposefully more pronounced in the illustrated embodiment as the depicted embodiments incorporate sensors on the front or leading end with tail fins on the tail section.

The longitudinal cylindrical vessel body was chosen as an illustrative example due to its hydrodynamics that provide minimal drag in comparison to other shaped bodies (to be discussed in greater detail below). However, it is readily understood that various shapes and sizes of a vessel body can be employed including spheroid (e.g., oblate spheroid), conoidal, rectangular, barrel-shaped, elliptical, ovaloid, oblong, circular, tubular, etc. It remains preferable that the body be designed to minimize drag caused by the current of the marine environment in which the device is to be employed. The drag affects the endurance of the device because energy needs to be expounded to counter its force, both in keeping the device stationary and, particularly, when adjusting the position of the device.

Figure 4:
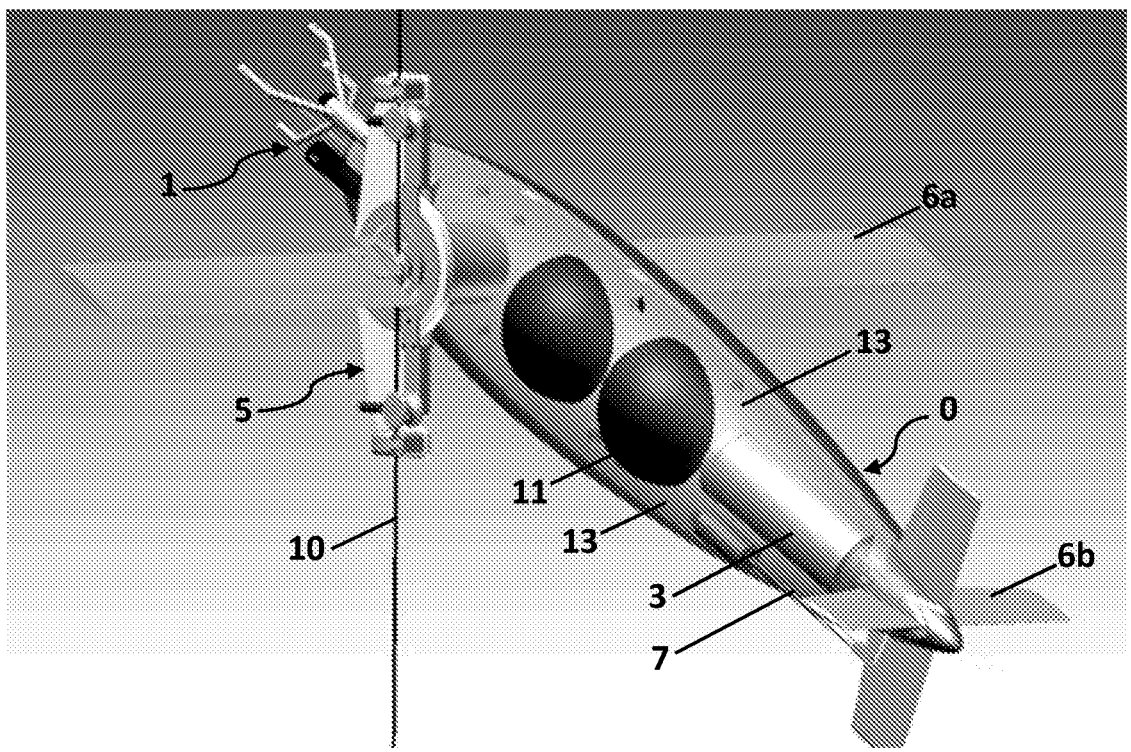
FIG. 4 is another illustrated embodiment showing a back side view of the components of an articulated moored profiler comprising a singular elongated vessel body that has been made transparent to show the inner components.
Figure 7:
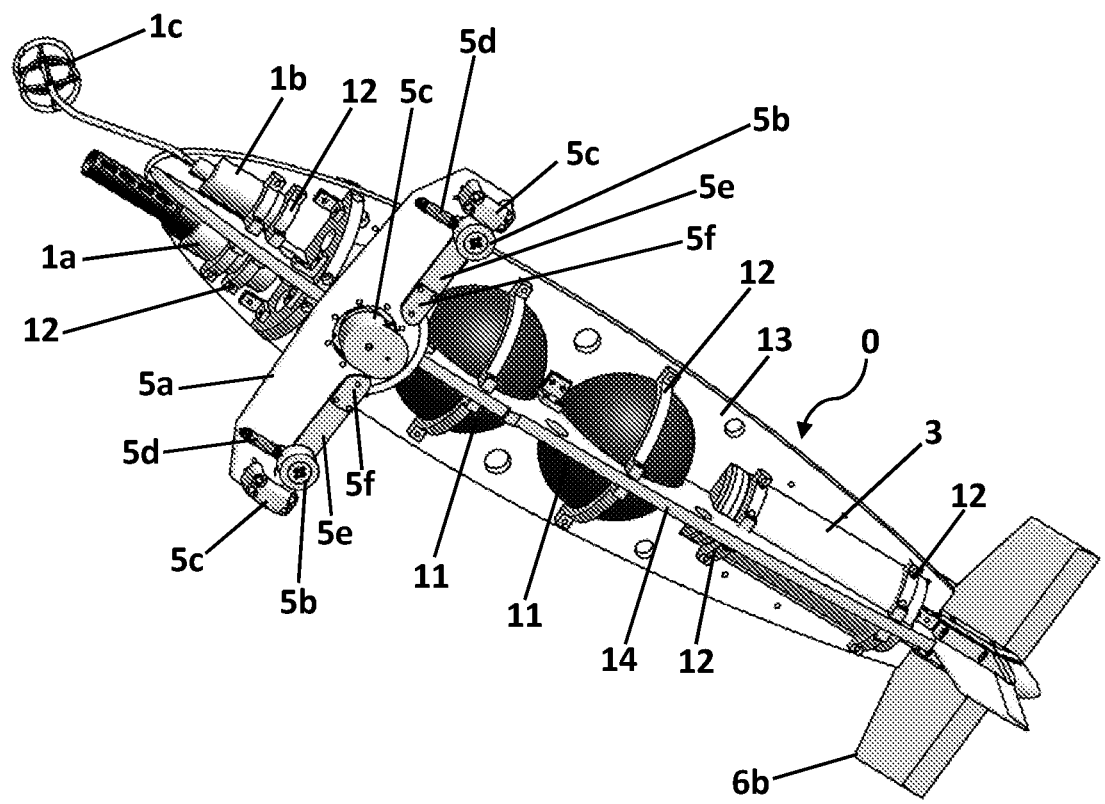
FIG. 7 is an angled side view of a three dimensional rendering of the schematic in FIG. 6.

The interior frame of the vessel body 0, in many embodiments, is designed with several factors in mind, including safely securing the internal components, robustness necessary for in stronger environmental conditions and increased pressure forces at deeper water depths, weight management, and manufacturing cost. As shown in FIG. 7, the interior frame is comprised of one or more vertical plates 13 and one or more horizontal plates 14 secured together at a desired angle. As depicted in the embodiment of FIG. 4, the internal frame may only comprise one plate, either a vertical plate 13 (as shown) or a horizontal plate (not shown). In the embodiment shown in FIG. 7, a vertical plate 13 and two horizontal plate 14 are mechanically engaged approximately 90 degree angles and secured using fasteners (e.g., nuts, bolts, pins, screws, or the like). This provides an optimal amount of internal space to include operating components and buoyancy means while maintaining a frame that can withstand up to full ocean depth. The internal frame may be manufactured from any material of suitable strength that can be matched to the buoyancy requirements including, but not limited to, aluminum, titanium, steel, stainless steel, steel alloy, thermoplastics, among others as known in the art.

The vessel body 0 further comprises a shell adapted to provide the streamlined body shape and maintain integrity of the internal components against water and pressure damage. The shell is further designed to employ a body shape capable of utilizing lift gained by use of the lift assist system 6. The shell is generally as thin as possible to reduce excess weight (and extra buoyancy compensation) while still meeting the necessary strength requirements for operation. The shell may be comprised of a top portion and a bottom portion wherein both the top and bottom portions are sealed together in a water-tight manner over the internal frame to create the streamlined body illustrated in FIG. 4. Similarly, the shell may be comprised of two or more lateral portions which are sealed water-tight. The shell is generally comprised of a thin yet durable material such as polyethylene (e.g., ultra-high molecular weight polyethylene), thermoplastic, or the like.

The purpose of the AMP is to take profiles underwater which typically includes repeated measurements of one or more parameters down and/or up through the water column. Thus, the AMP employs a sensor array 1 of one or more sensors to take measurements and readings while in operation. Dependent on the particular mission on which the AMP employed, numerous sensors may be useful under the circumstances and specific applications that allow for the collection of readings on temperature, location, conductivity, salinity, magnetics, depth, current, gravity, oxygen, carbon, nitrogen, or light (e.g., fluorescence, bioluminescence), to name a few. Thus, thermometers, magnetometers, hydrometers, radar, depth sensors, pressure sensors, gravitometers, oximeters, light meters, fluorometers, GPS, seismographs, Geiger counters, current meters, CTD's (conductivity/temperature/depth), acoustic current meter (ACM), and salinometers may be mounted to the vessel body 0 (or the attachment mechanism 5) such that they can be employed during operation. In other embodiments, the AMP is designed to house any of the numerous sensors currently employed on moored profilers from the prior art. For example, the sensors may also be selected from the group comprising the Seabird 52MP CTD, Teledyne RDI Micro CTD, Falmouth Scientific current meter, Nobska modular acoustic velocity sensor (MAVS), Seabird 43F dissolved oxygen sensor, Satlantic Submersible Ultraviolet Nitrate Analyzer (SUNA), Nortek Aquadopp current meter, Seabird Inductive Modem, Biospherical Instruments Photosynthetically Active Radiation (PAR), WET Labs Optical Sensors, Seapoint fluorometer, Seapoint turbidity sensor, Aanderaa optode, the OceanServer motion sensor, or any later generations thereof. In some embodiments, the device employs one or more sensors to sample aspects or features of the body of water such as conductivity (e.g., salinity), temperature, depth, light level, turbidity, dissolved gases (e.g., oxygen, nitrogen), fluorescence, bioluminescence, pressure, pH, a chemical, radioactivity, water currents (e.g., meandering currents, eddies, rings, hydrographic fronts, rip currents, feeder currents, tides) and any measurable parameter of the water. In some embodiments, the device is capable of taking water samples from the environment for analysis at a later time.

Figure 6A:
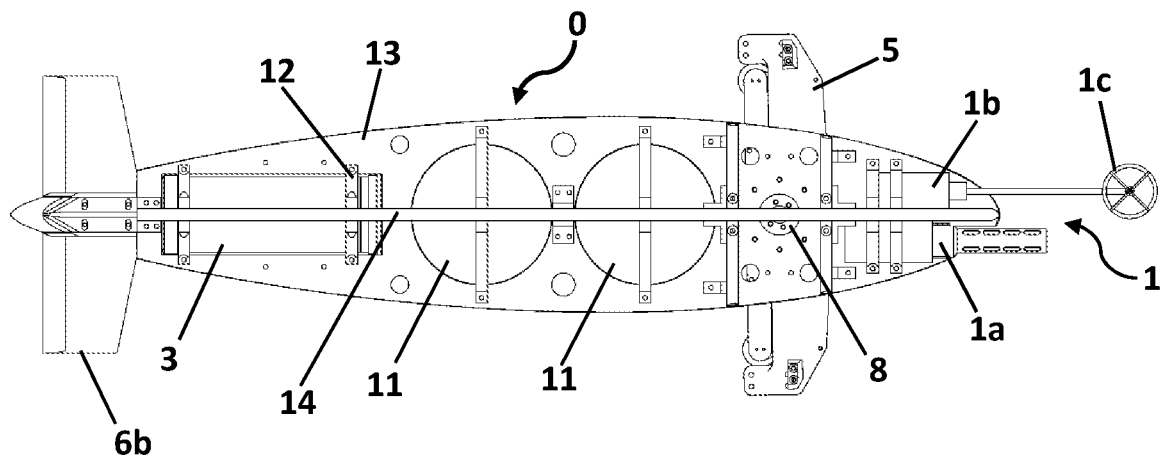
FIG. 6A is a view form the port side and FIG. 6B is a view from the starboard side.
Figure 6B:
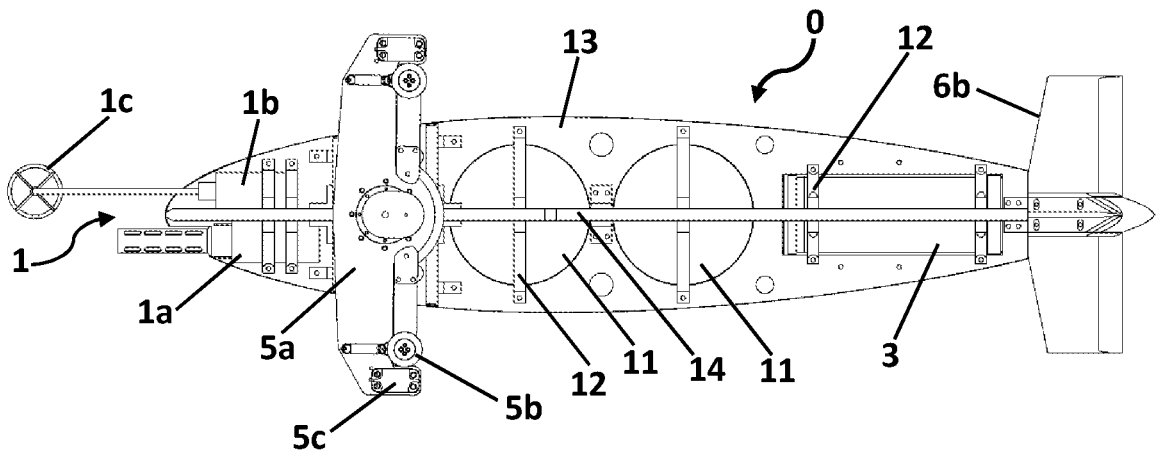

As existing models often struggle to arrange the sensors and the drive system at the mid-point of the profiling vehicle, the depicted embodiments of the AMP device separate the drive system 2 from the sensors 1, and moreover, naturally orients the sensors 1 at the leading end of the body 0 to allow sensing in undisturbed water (i.e., water which has not been altered by the presence of the device, water in its naturally occurring state). This adaptation also provides more flexibility in mounting multiple sensors such as bio-optical devices in addition to a CTD and current meter. Further enhancing the abilities of the device is the new controller 4 which facilitates the addition more sensors of various types. Additionally, placing the sensor array 1 at the leading edge of the vessel body 0 facilitates operator access for maintenance, sensor adjustment, or repair. In other embodiments, the sensor array 1 is disposed on the aft or trailing end of the device. In another embodiment, the sensor array 1 is arranged at one or more positions on the leading end, trailing end, or the middle region of the vessel body 0. In many embodiments, one or more sensors in the sensor array 1 are mounted at the leading end of the body to sample undisturbed water. As depicted, the sensors 1a and 1b are housed in a compartment in the leading end of the longitudinal vessel body 0. Sensor input 1a is a collection tube that projects from the front of the longitudinal body 0 to allow for fluid to pass into the sensors. These sensors 1 are in electronic communication with a power source 9, which is typically a battery. In the depicted embodiment of FIGS. 6A and 6B, a sensor rod 1c connected with sensor 1b further protrudes from the leading end of the AMP to measure water current.

As depicted, embodiments can be utilized wherein a water sample will enter the sensor compartment. Thus, it may be desirable to separate the sensors 1 from the electronic controllers 4 and power source 8, which are depicted to be located it the electronics housing 3 in the aft section of the vessel body 0. Electronics housing 3 is a container in which one or more electronic devices such as the controller 4 and power source(s) 8 can be housed. It may be pressurized and/or waterproof depending on the embodiment and mission. In several embodiments, the electronics housing 3 is a pressure housing with a depth rating of up to 6,000 m. In another embodiment, the electronics housing 3 is rated to depths greater than 6,000 m. The housing 3 is generally comprised of a robust material such as metal including titanium, aluminum, steel, or other suitable materials as known in the art. Balancing the device for buoyancy reasons may also dictate the location of the power source and controller in relation to the sensors, although it is conceivable that an AMP can be made wherein one or more sensors, power sources, and controllers, can be placed throughout the vessel body either in electronic communication with each other or otherwise in insular systems.

Figure 8A:
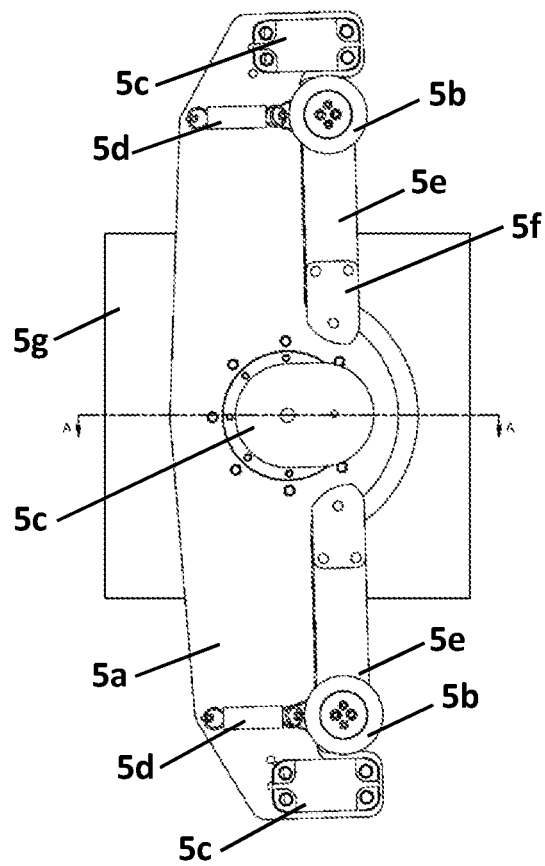
Figure 8B:
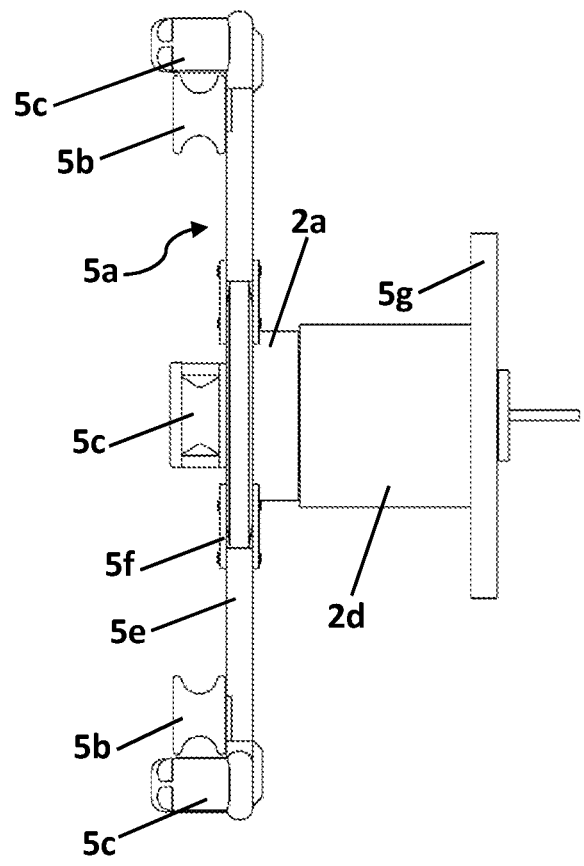
FIG. 8B is a side view and FIG. 8C is an angled view of the same attachment means.
Figure 8C:
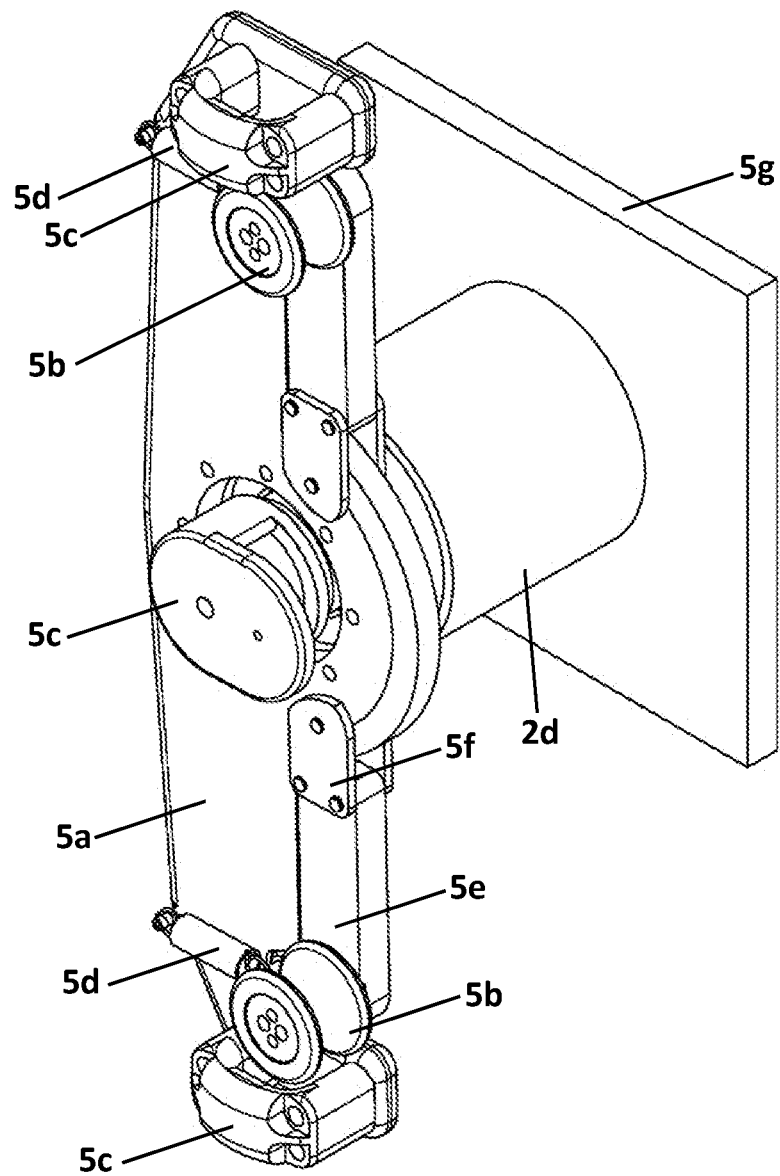
Figure 9A:
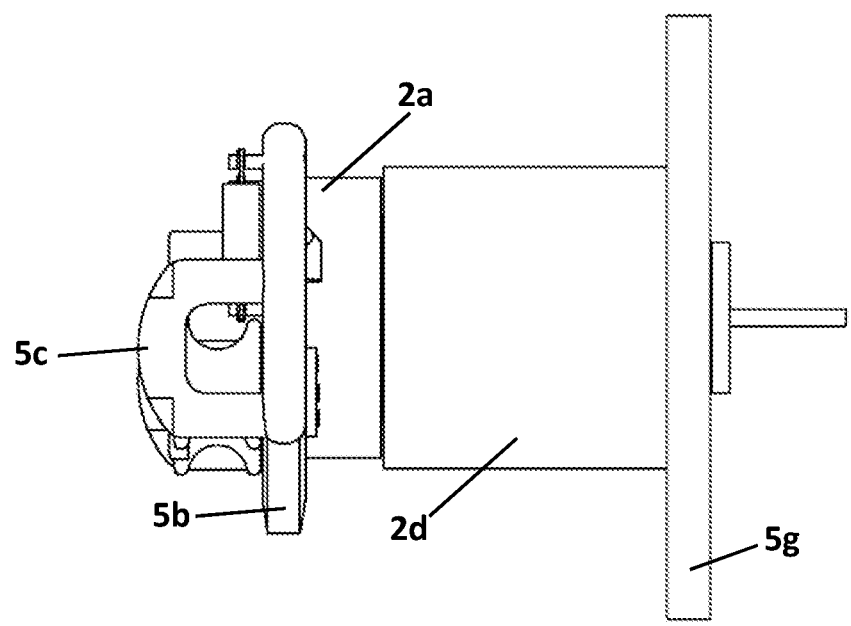
FIG. 9 shows the outer casing of the drive means in FIG. 9A and a cross section view of the inner components in FIG. 9B.
Figure 9B:
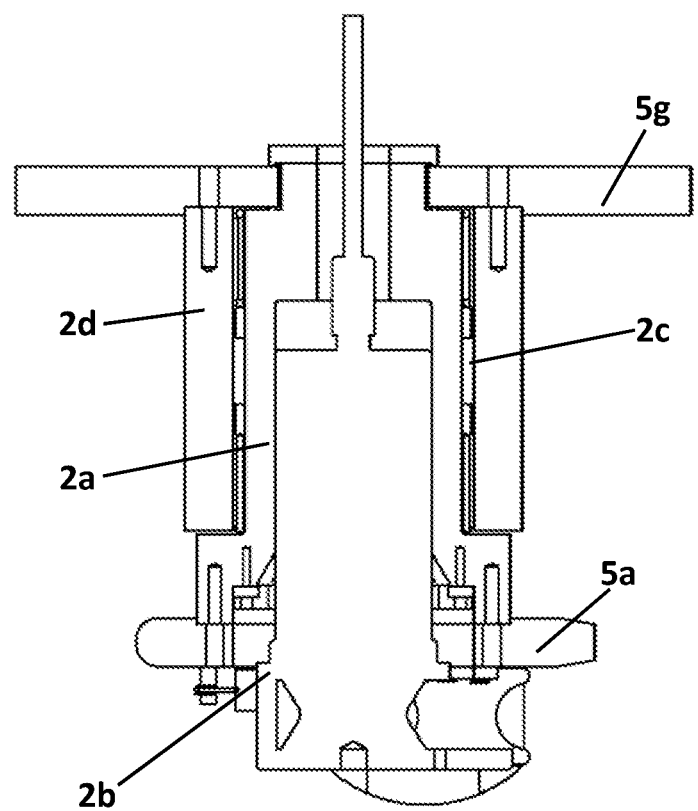
Figure 10:
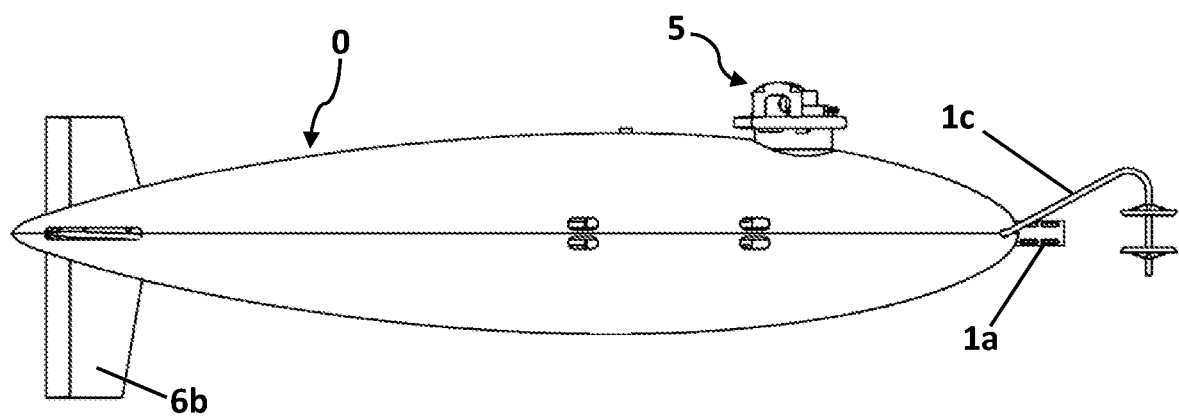
FIG. 10 is an illustrated embodiment depicting top down view of the vessel body.

As a moored profiler, the AMP is connected to a mooring wire 10 as would be recognized by one having ordinary skill in the art and as further shown in FIGS. 1-4. Turning to FIGS. 8 and 9 specifically, a mechanical drive assembly 2 is employed wherein the mechanical drive assembly 2 comprises a drive engine 2a that mounts on the wire 10 via an attachment mechanism 5 whereby the main vessel body 0 is supported by the mooring wire. As will be explained, the vessel body 0 is connected to the mooring wire 10 through the tension created as the mooring wire 10 passes through a plurality of grooved wheels (the drive wheel 2d and the guide wheels 5b).

Attachment means 5 comprises a longitudinal truck plate ("truck") 5a, at least two guide wheels 5b, and a set of one or more cable guides 5c. The truck 5a is a longitudinal plate on which the guide wheels and cable guides are mounted and able to withstand the forces on the cable particularly in strong current conditions. The cable guides 5c comprise brackets orthogonally connected to the truck 5a on opposite ends of the longitudinal truck 5a through which the mooring wire 10 is passed. It is preferred that the hole in the cable guides be lined with a material to soften impact with the mooring wire, thereby limiting the potential to fray the wire (when the wire is made of a material susceptible to fraying). In some embodiments, the cable guides and/or guide wheels are coated with a protective material such as urethane, polyurethane, organic polymer, inorganic polymer, thermoplastic urethane, oil, and other lining materials as known in the art. The guide wheels 5b are connected to the truck 5a via idler arm support 5e in substantial proximity to and on the interior side of the cable guides 5c. The idler arm support 5e is attached to the truck 5a by an idler arm tab 5f to provide pivoting support for the attachment mechanism 5. These guide wheels 5b act as both stoppers and retaining rings capable of retaining the device in a stationary manner on the mooring cable 10. The guide wheels 5b are connected to the truck by tension springs 5d that pull the guide wheels 5b towards the drive wheel 2d, thereby keeping tension on the mooring wire 10. In one or more embodiments, the tension springs 5d can controllably be manipulated to increase or decrease tension on the guide wheels, such as may be needed to act as a brake or to lock the unit in place. Additional grooves can be formed in the wheels 5b and 2d to help grip the mooring wire. The mooring cable 10 may be any suitable cable or line of sufficient strength properties to serve as a connection to the bottom of the water column.

The drive wheel 2d is positioned substantially in the center of the truck 5a and is manipulated by a drive engine 2a that is capable of rotating the drive wheel to maneuver the vessel body 0 up and down the mooring wire 10. The drive engine 2a is mounted through the attachment mechanism 5 such that a substantial portion of the motor 2b sits on the vessel body side of the truck 5a, but remains connected to the drive wheel 2d. The drive engine 2a is positioned forward of the mooring wire with the drive wheel axel orthogonal to the vessel body axis. The drive engine 2a uses an electric motor 2b in a dedicated pressure vessel 2c that turns the drive wheel 2d on the opposite side (held in tension against the mooring wire 10) using a magnetic coupler across the pressure case wall. The magnetic coupler can be further employed as a brake by locking the drive shaft of the motor.

The attachment mechanism 5 may be further modified by adding a cowling or a cover over the outer face of the mechanism 5. This serves several purposes including further drag reduction, less component biofouling, and additional impact protection of the mooring attachment components. In some embodiments, the cowling covers the truck plate components while still allowing flushing of biological material from around the components (e.g., drive wheels). In some instances, the truck plate 5a (and other components exposed to the surrounding environment) may be coated with an antifouling paint or other coating which prevents organisms and marine debris from attaching to the surface and building up.

A key advantage of the present invention is the ability to manipulate the vessel body 0 both to align the vessel body 0 with the relative three-dimensional incident flow, thereby reducing drag, and to align the sensors 1 such that they are able to sample undisturbed waters. Additionally, the system is designed to align relative to the current flow to harness the flow forces to thereby assist the system in profiling upward to minimize power consumption. Existing profiler models have struggled to perform in the face of the drag forces exerted upon the profiler body and vortex shedding when attempting to operate in strong current environments, causing the profiler to lose traction, fail to profile over the programmed depth interval, and deplete the power source prematurely. The instant AMP solves this problem because the longitudinal vessel body 0 is able to articulate about the mooring wire 10 to align with the relative three-dimensional incident flow. As depicted, the improved Articulating Moored Profiler incorporates an articulating mechanism 8 that allows the hydrodynamic body of the profiler to rotate, pivot, and align both horizontally about a cable and vertically in response to the three-dimensional incident relative current flow past the profiler. Depending on orientation, the longitudinal body may need to either be able to articulate vertically or horizontally (or both) about the mooring wire 10 to align with the relative three-dimensional incident flow, so it is important for the pivot mechanism to be able to accommodate the articulation needed for the set up. In certain embodiments, the articulating mechanism 8 allows the vessel body 0 to articulate 360 degrees horizontally about the mooring cable 10. In various embodiments, it may be desirable for the AMP to be able to pivot ±90 degrees about its attachment point to the truck 5c that supports the drive and spring-mounted guide wheel sheeves. In certain embodiments, the vessel body 0 is able to articulate substantially vertical up to ±90 degrees relative to the mooring cable 10. In other embodiments, the articulating mechanism 8 may be adjusted to only allow the vessel body 0 to pivot to a designated degree relative to the mooring cable 10 such that the body may only up to an angle of 45 degrees, 60 degrees, and so forth in one or both vertical (up/down) and horizontal directions.

As depicted, the articulating mechanism 8 comprises a lockable and rotatable bracket or gear connected to both the vessel body 0 and to the attachment mechanism 5, generally through or in proximity to the drive motor assembly 2. Numerous types of hinges, brackets, ball joints, and other connected may be employed that are capable of allowing a pivot action between the vessel body 0 and the mooring wire 10. As the AMP adapts, either by active or passive manipulation, to provide the most efficient position to reduce drag in these strong flow environmental conditions or to orient sensors as may be desired, these forces have substantially less effect on movement control and reliability. By orienting into the relative flow, the AMP also improves the quality of data from sensors mounted on its leading end. Any wakes from the mooring wire or vehicle body are downstream from the sensing volume of the probes so the water being sampled is relatively undisturbed.

Typically located in the aft end of the longitudinal vessel body 0 is a power supply 9 in the form of a battery to power the sensors and the drive means. It should be noted that the AMP is designed to be used in marine environments and therefore pressure will be exerted on the unit and its components. This can be particularly detrimental to batteries and smaller electronics so it can be advantageous to employ pressure case(s) for batteries and to adapt the main controller for deep water (e.g., up to 1,000 m, 3,000 m, 6,000 m, 6,500 m, 8,000 m, and full ocean depth). The device may employ a main power source and additional battery packs for backup power. In some embodiments, the power supply 9 is a rechargeable battery such as a rechargeable lithium battery; however, the power supply may include any suitable power source that can power the device through profiling completion either with or without the use of the lift assist system 6 described in more detail below.

Energy efficiency is a large problem in underwater profilers as the power generally has to be provided onboard the vessel, particularly when the vessel is to be deployed at great depths. Thus, to increase the profiling endurance of the unit in operation, the AMP further incorporates, in one or more embodiments, numerous energy saving mechanisms. Endurance is defined by the distance of cable traveled by the profiler during a mission. The articulating mechanism 8 in combination with the streamlined vessel body 0 has substantially increased endurance to about 2 million meters, double of previous profiler endurance. Additionally, the lift assist system 6 further adds to the device endurance as well as increases battery usage which may be applied to longer profiling missions, more sample measurements, and/or additional or high power-consuming sensors.

One of the more promising energy saving mechanisms is through the incorporation of a lift assist system 6. As depicted, the lift assist system 6 comprises at least one of a wing set 6a and a fin set 6b (e.g., adjustable wing set, adjustable fin set). Several embodiments of the inventive system employ both a wing set 6a and a fin set 6b. Additional embodiments may utilize more than one wing set 6a and one or more fin sets 6b. In other embodiments, the device comprises a wing set 6a or a fin set 6b. In additional embodiments, the device comprises a lateral fin set arranged laterally on the vessel body 0 in an orientation adapted to be controlled by the lift control system 7 or in a fixed orientation.

Figure 5:
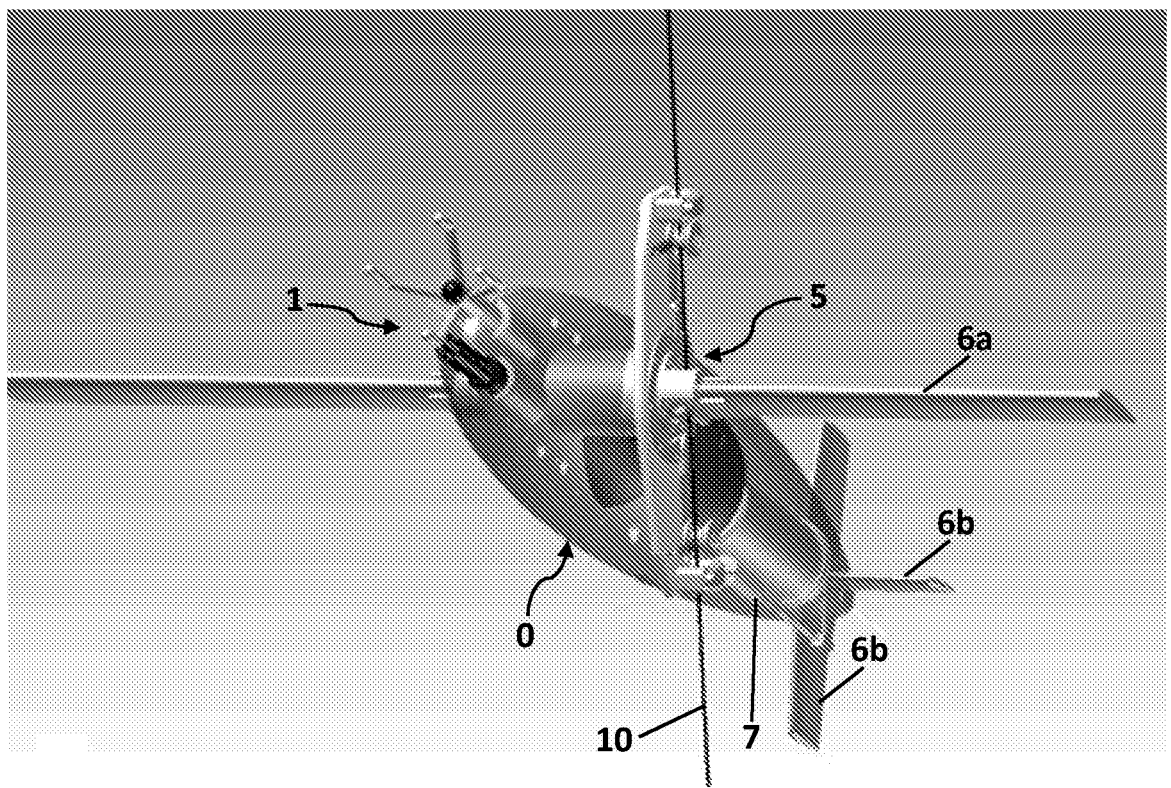
FIG. 5 is a front angular view of the same embodiment as in FIG. 4 to further illustrate components of the embodiment.

As shown in FIGS. 4 and 5, the wing set 6a is arranged forward on the vessel body 0 aligned with the attachment mechanism 5. In other embodiments, the wing set 6a is arranged near or at the middle section of the vessel body 0. The wing set 6a may be controlled by the drive motor assembly 2 or lift control system 7 to obtain the optimal angle of attack for propelling force or in other cases may be securely attached in a fixed orientation at a specified angle using fasteners.

The AMP device further aims to increase profiling endurance (as well as reliability) by using lift foils and/or employing a body shape in various embodiments to gain lift from the incident ocean currents to assist the drive motor(s) in propelling the vehicle up and down the mooring wire. It is exactly during these periods of strong incident ocean currents that existing profilers have difficulty profiling whereas the present invention harnesses these currents to extract lift which reduces power consumption. However, it is not just these extreme events that are of interest; due to tides, internal waves, and mesoscale motions, there is high probability that incident ocean currents of several cm/s or more will always be present at a given mooring site, depth, and time. Any lift that can be gained from the ocean flow is, in effect, "free" energy. The AMP system orients wings (e.g., fins) and/or a lifting body-shaped vehicle relative to the three-dimensional incident flow to obtain an assist when moving along the wire and/or to help maintain a depth while resting between profiles.

Lifting foils in the shape of wings 6a or fins 6b to extract lift out of the current, effectively harnessing "free" energy that saves battery power and extends operational life of the AMP. In one or more embodiments, the AMP employs a wing mechanism (e.g., one or more fins, wing set 6a, fin set 6b) to harness the forces of strong incident water currents and translate these forces into vertical movement to propel the device vertically along the mooring wire. Beyond improving performance at times of strong water currents (a shortcoming of existing systems), the capacity to utilize environmental energy allows the profiler to use less battery-derived energy, thus extending the endurance of the device and/or allowing the integration of higher energy-consuming sensors or the more frequent use existing high energy-consuming sensors. In the uni-vessel embodiments shown in FIGS. 4 and 5, symmetric-profile wings 6a are applied to the AMP vessel body 0 and a controller-adjustable "elevator" tail fin 6b is employed to set the vehicle pitch and thus adjust the altitude of the wings to the incident relative flow. By "elevator" tail fin, it is shown that the tail fin set 6b of the lift assist system 6 is attached to the lift control system 7 which in this embodiment is a hydraulic piston that manipulates at least one tail fin up or down to adjust the amount of draft it catches from the current, referred to as the angle of attack. The angle of attack is a common term in the art to describe the angle of a fin or wing relative to the incoming incident current flow. In certain embodiments, the angle of attack is 1 degree, 2 degrees, 3 degrees, 4 degrees 5 degrees, 6 degrees, up to 10 degrees, up to 15 degrees, or up to 20 degrees relative to the flow.

Figure 3:
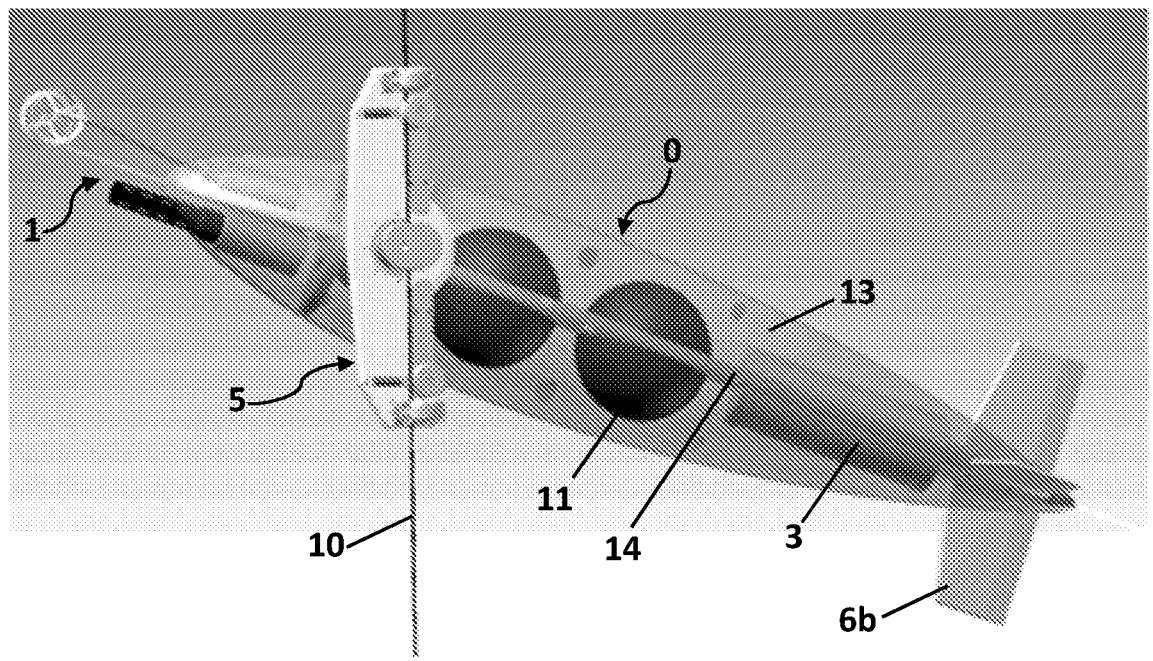
FIG. 3 depicts one illustrated embodiment of the articulated mooring profiler comprising a single body disposed on a mooring cable.

As shown in FIG. 3, the fins 6b positioned on the aft end of the vessel body 0 perpendicular relative to the body. In certain embodiments, the fins 6b on the top and bottom surfaces of the vessel body 0 are angled by a few degrees (i.e., angle of attack) to compensate for the off-center attachment to the cable 10 by the attachment mechanism 5.

Example 1 further describes key aspects of the lift assist system and angle of attack. This can be used to controllably utilize the lift provided by the current. Although the wings 6a are generally designed to work in concert with the drive motor assembly 2, it is conceivable that enough lift can be generated in certain embodiment so AMP such that the AMP can be maneuvered with little to no energy being employed to the drive motor assembly 2. Other embodiments employ other means than a hydraulic piston in the lift control system 7 including a mechanical actuator, linear actuator/positioner, electric motor, and any other mechanism to reliably and accurately adjust the angle of attack of the lift assist mechanism 6 preferably within an accuracy of a degree or less.

The compromise between adding battery capacity and the added drag due to the associated increase in instrument size is a necessary consideration. Various embodiments likewise utilize a controller 4 that is designed to reduce the energy consumption of taking measurements. For those deployments that require a real-time data telemetry capability, significant energy savings can be achieved with data compression as smaller files means less energy is needed for the transmissions. Existing profilers employ a controller which is not powerful enough to provide data compression of acquired measurement data. In one embodiment, the AMP device utilizes a Linux controller. Specifically, the inventive device employs a compound processor system which comprises a low-power microcontroller mated with a Linux controller, providing significantly more capability than the microprocessors used in existing profilers and with equal or less power consumption. Modems, antennas, radios, and other telemetry devices may be employed in conjunction with the sensors to transmit data from the AMP to an external source. In some embodiments, the telemetry means uses Iridium communication technology to transfer data from the device. The telemetry means may also employ acoustic communication via an acoustic modem/transducer.

A low-power microcontroller is interfaced to the external sensors 1 that are configured to either export data at a specified rate or respond to requests for a scan of data. Data collected will be time-stamped and temporarily stored in a buffer made up of one or more FRAM chips. At predetermined or regular interval, the controller 4, which is a Linux controller, will wake up, extract, and archive the sensor data (while new data is acquired to a second buffer) and perform whatever other instrument control functions that are required before returning to low-power sleep mode. The microcontroller will have provision for multiple digital and analog sensor inputs. Time-stamping the sensor data greatly simplifies the processing of the data in comparison to the process of logging conductivity/temperature/depth (CTD), acoustic current meter (ACM), and engineering plus analog sensor data in separate files with no common reference variable to align the CTD and ACM scans (an ad hoc scheme referencing the start and stop transients of each profile is used to data) as done in previous profiling systems.

In one embodiment, the Linux controller is essentially a break out board (baseboard) for the Technologic Systems TS-4200. The TS-4200 is a high performance low power 400 MHz Atmel AT91SAM9G20 ARM9 with 64 MB or 128 MB RAM. The baseboard takes in a nominal 12V supply and produces 5V and 3.3V at better than 90% efficiency. The base board optionally brings out 10/100 Ethernet and USB as well as five RS232 serial ports each with 12V or 5V switching capability. The system will support two more ports that will provide console connection (operator interface) and communications to the supervisor chip. The supervisor uses a Real Time Clock (RTC) to make decisions about when to wake the Linux system. The supervisor also has two logic level or RS232 comm ports used to communicate to the CTD and drive motor board. The motor board also has a low power microchip that is off or in very low power state most of the time. As noted above, two 1 Mbit FRAM chips may be used as a ping pong buffer for real time data buffering. The motor board has a motor driver to control the profiler drive wheel in both directions and with PWM (pulse width modulation). The motor board also has 4 channels of 16 bit ADC or 2 differential channels. The motor board supports an additional 4 serial ports at Logic or RS232 levels by utilizing Quad SPI UART chip. These 4 ports have hardware flow control capabilities and also support switching 12V power to each port. It is important to note that these 4 ports are available via SPI bus to the main supervisor not the motor board micro. The motor board micro is tasked with all motor functionality, voltage and current status, transceiver switching, port power switching and the 16 bit ADC measurements. The motor board will measure voltage and current for the motor and sensor loads separately.

Equally important in many ways to the goal of increasing profiling reliability is the goal of increasing profiling endurance. In one embodiment, profiling reliability is addressed by first reorienting the drive assembly and guide wheels (as compared to the prior art) to fore-aft orientation with the drive wheel on the upstream side of the mooring wire. As the horizontal drag forces on the profiler increases with the strength of the incident horizontal ocean currents, this increases the pressure of the drive wheel on the wire and increases traction (ocean current drag forces on the existing profiler's athwartship-oriented motor causes the wire to ride up one cheek of the drive wheel, which reduces traction and profiling reliability). The AMP device employs a subsystem (operated by the main instrument controller 4) to increase drive wheel 2d tension on the mooring wire 10 by, for example, pulling harder on a tension spring 5d, if it is judged that more traction is required. Other embodiments utilize two drive wheels (both upstream of the wire) and one guide sheeve for this purpose of increasing traction. While this method will use more energy than the present one motor, the energy drain will not be doubled, and it will certainly enhance profiling reliability.

An instrument control program is designed to run the AMP device which allows users to select which sensors to operate on each measurement cycle. This is particularly advantageous over previous models in which all of the sensors configured for a given deployment are operated on every measurement cycle, consuming substantially more power than necessary. The flexibility in sensor operation allows for long-term deployments of high energy consumption sensors by running the sensors on a subset of measurement cycles or only over selected depth ranges. Use of a more capable central controller additionally allows the device to acquire and log more diagnostic information about the system performance than was previously possible. Specifically, rather than make motor electrical current and battery measurements at several second intervals, quantities such as motor current as well as record peak values can be oversampled and averaged. In addition, the drive motor assembly 2 and guide wheels 5b may be instrumented to track their rotation to assess wheel slipping. This information may be fed back to the active system controlling drive wheel tension on the mooring wire 10 to increase efficiency.

But, more drive wheel tension against the mooring cable to increase traction will likely incur greater motor energy drain. Thus, another approach in the endurance area is streamlining to reduce drag. The longitudinal vessel body design of the inventive device targets this concept, as do design efforts to reduce the cross-sectional area of the profiler, including using smaller-diameter buoyancy spheres 11 than those in existing profiler models, and/or using syntactic foam and possibly containers of buoyant compressible fluid as mentioned above. While buoyancy compensation is accomplished by the buoyancy sphere(s) 11, buoyancy may be managed by any other shape of a suitable volume to be housed in the device. Many embodiments of the present invention utilize a sphere as testing has shown this model to meet several necessary criteria including suitable volume, device buoyancy requirement, and cost/ease to manufacture. The buoyancy sphere may be comprised a material such as glass, ceramic, plastic (e.g., thermoplastic), foam, aluminum, titanium, and any other material as known in the art for buoyant properties or creating buoyancy. While two buoyancy spheres 11 are shown in the figures, in some embodiments, the device buoyancy can be managed by one sphere 11 or multiple (e.g., more than 2, 3, 4, 5, 6, or more) spheres 11 to allow the device to have a substantially neutral weight in the water column.

In previous models, the buoyancy spheres 11 served also as electronics housings. While some embodiments of the present invention can be modified to house the electronic components within the buoyancy spheres 11, the improved AMP design typically uses a separate electronics housing 3 to protect the electronic components from water damage. Doing so substantially improved the design as the electronics housing 3 is now easier to service by the operator, and the migration of the electronics to the aft end of the vessel body 0 balances the internal components for optimal articulating movements. Even in cases where the cross-sectional area of the AMP device is larger than existing profilers, this does not necessarily result in greater total energy use as a result of the balanced design. Additionally, relocation of the electronics to the electronics housing 3 has also increased internal space which was previously unavailable due to additional wiring and connections with the spheres.

To ameliorate ballasting errors, an active system to jettison small weights heavy and/or buoyant pellets can be employed to trim instrument buoyancy after deployment (and possibly periodically during a mission). To even out buoyancy forces during profiles, use of a buoyant, highly-compressible fluid in a deformable container may be used, which can be housed within buoyancy spheres 11. The volume change with pressure helps compensate the buoyancy forces that develop as the vehicle moves through the ocean's in situ density stratification. The vehicle body design to extract lift from the incident horizontal currents to assist the drive motor(s) is described more below. A robust mechanical design that is able to withstand and perform in the face of significant mooring wire strumming is used to further enhance the reliability of the device.

Another feature of certain embodiments of the present invention includes a system which allows the profiling vehicle to detect physical stops on the mooring cable which may be placed to prevent the vehicle from running into the mooring wire terminations and becoming stuck. Existing profilers check their measured pressure against pre-programmed limits and change in pressure over time (dP/dt). In cases where a mooring happens to be deployed at a depth different from the design (or ocean currents cause blowdown of the mooring), it is possible for the profiler to impact the wire stops on each profile and grind its drive wheel until the system terminates the profile based on when dP/dt equals zero. This grinding wastes energy and can polish the drive wheel, causing reduced traction over time. In some embodiments, a magnetic or optical detector and/or a system monitors the guide sheave turning rate as a complementary wire stop detection method to dP/dt equals zero.

The improved AMP device enhances the user interface to reduce problematic deployments caused by operator error. A braking system is employed to hold the position of the AMP on the mooring wire between profiling operations. As noted earlier, the braking system of the existing profilers allows slow drift of these vehicles along the wire. One approach is a lock on the driveshaft of the motor(s). This approach, housed inside the motor pressure case, relies on the magnetic coupler to lock the drive wheel and in turn, brake the vehicle. Another method uses a device to physically clamp the mooring wire. Such a device provides additional insurance against vehicle loss in the event the mooring wire breaks between stops on the wire. In some embodiments, the braking system is capable of decelerating, stopping, and/or holding the device at a selected location in between profiles (e.g., programmed vertical route).

Example 1

The drag of the AMP was estimated and compared to estimates of the drag of the McLane Moored Profiler ("MMP") from the prior art. The drags were estimated for a state with 30 cm/s current while the profiler is traveling along the mooring cable at 30 cm/s. Much of the drag of the MMP and most of the drag of the AMP is from the bluff cable guides, guide wheels, drive motor, CTD, and acoustic current sensor. When there is zero current, these bluff bodies are in line, and the downstream bodies are in the wakes of the upstream bodies, reducing drag. When the current is 30 cm/s, each bluff body is in fresh flow and does not benefit from wake shading.

The total MMP drag is estimated to be 8.6 N of which 6.1 N is in the direction of profiler movement. The MMP body drag is estimated to be 3.8 N. The AMP as described herein used a low-drag body in the longitudinal vessel body 0, which is streamlined and pointed into the flow, keeping the boundary layer attached. The bare body is estimated to have a drag of 0.2 N. The bluff bodies of the cable guides, guide wheels, and motor are estimated to have the same high drag as on the MMP. The term "bluff" is used here in the nautical context to mean having a full, blunt form. The truck plate of the AMP is bluff and adds drag over that used by the MMP design, but the acoustic current sensor and CTD sensor can be aligned into the relative flow reducing their drag. For this reason, the total AMP drag under these conditions is estimated to be 3.5 N in the direction of profiler travel. The body drag has been significantly reduced, but the bluff body drag is basically the same. In the past, it has been noticed that streamlining the cable guides, guide wheels, and drive wheel in a shroud can result in fouling from filamentous material in the ocean (often fishing line). However, additional research and improvements to reduce the drag further while providing fouling resistance of the truck may be performed.

The AMP was designed about a 30 cm/s current while the profiler is moving 30 cm/s on the mooring cable. The wing area of 0.387 $m^2$ was designed to lift four times the drag, further enhancing the streamlined feature of the AMP, corresponding to the peak observed motor current of 250 mA. The wing has a National Advisory Committee for Aeronautics (NACA) 0018 foil design and with a 6 degree angle of attack at the relative flow of 42 cm/s should give a lift of 21.3 N. This thick foil was chosen for strength, effective lift in both directions, and tolerance of twice this angle of attack before stalling. This factor of four was chosen to tolerate significant mooring cable angle from vertical, when the lift vector is a large angle away from the cable and profiling direction.

Figure 11A:
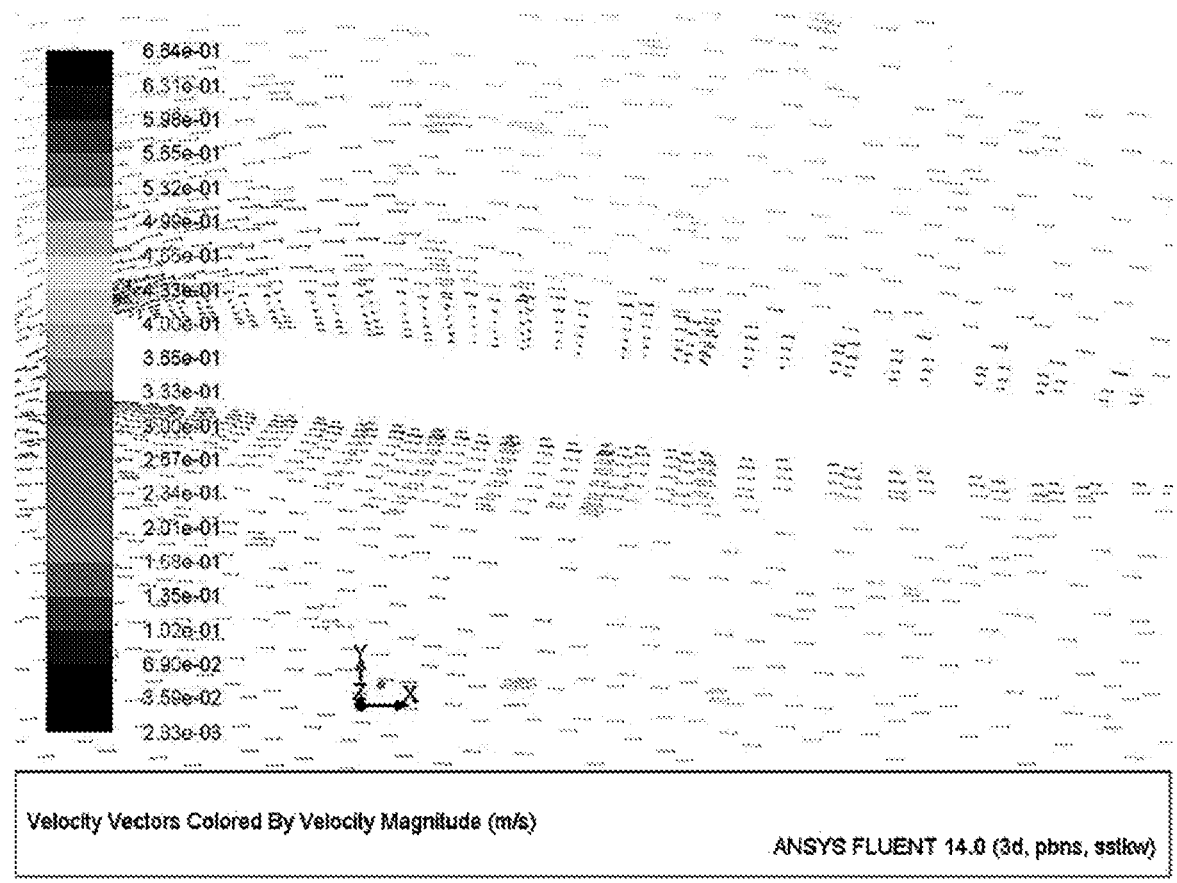
FIG. 11A illustrates the flow model of the existing fin.
Figure 11B:
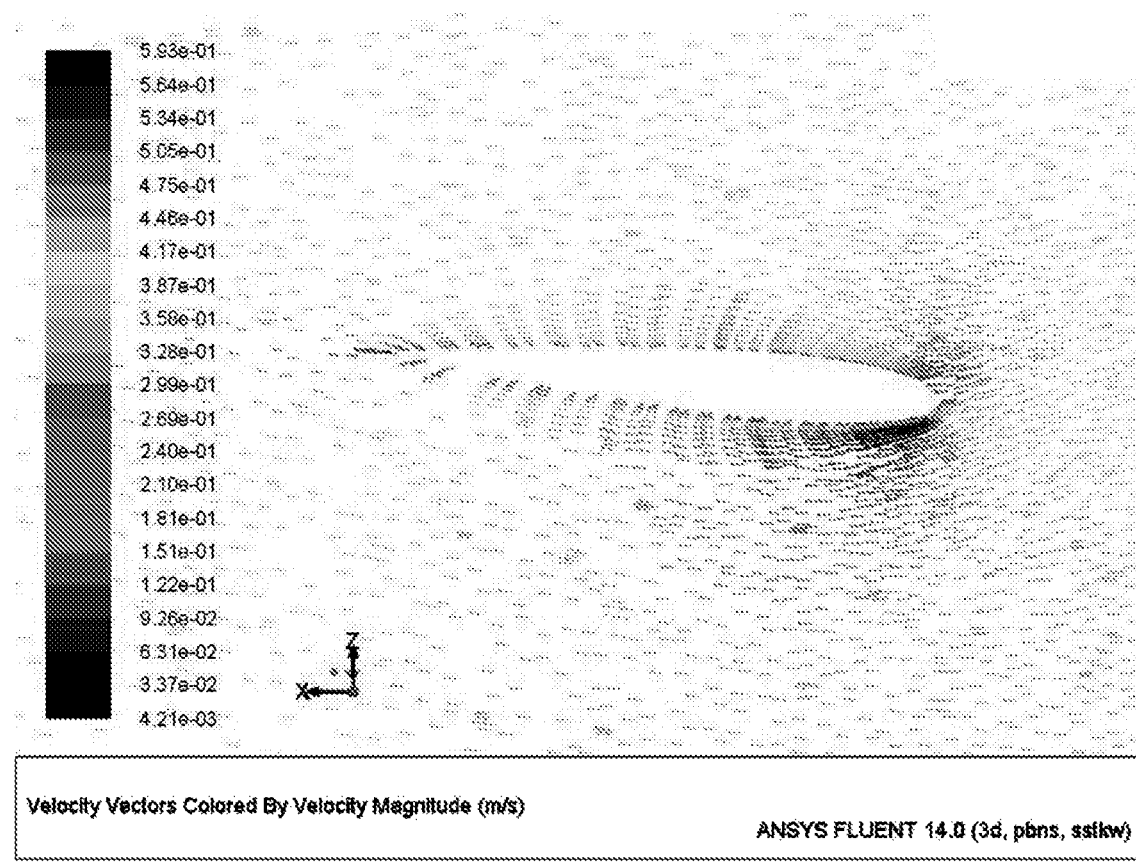
FIG. 11B illustrates the flow model of the streamlined fin design.

Additional modeling is being performed of the flow over the profiler using Fluent. The original design for the tail fins, using a shape that was convenient to machine, stalled at 5 degrees angle of attack, FIG. 11A. By changing the fin shape, to the more involved to machine NACA 0012 foil, the stalling at 5 degrees angle of attack can be avoided, FIG. 11B.

The proposed AMP device will be well-suited to support at least two general areas of ocean observing in future. The first is ocean time series stations: long-term observations of water properties and currents at a fixed geographic site. Greater endurance and improved reliability of the AMP relative to current technology can only benefit these measurement programs. The second class of study focuses on ocean fine structure—those processes that have direct relationships to turbulent mixing. One such process is the breaking of internal lee waves: motions that are generated when sub-inertial flows encounter bathymetric features such as ridges and seamounts. Being specifically designed to function better in strong ocean flows than the current technology, the AMP will be a natural tool to investigate lee wave generation and breaking.

One deployment mission of the AMP device has been drafted to carry out the proposed instrument testing and development. The mission timeline is built around a proposed 6-month trial deployment of the AMP at Line W mooring site #5: 38° 5' N, 68° 41' W in 4,100 m water depth. This site periodically experiences upper ocean currents well in excess of 1 m/s associated with northward meanders of the Gulf Stream and associated Warm Core Rings, which has been considered unsuitable conditions for the MMP, and as such will present an opportunity for operation of the AMP. The mooring consists of a 4,000-m run of mooring wire with current meters and temperature/conductivity sensors fixed on the mooring at the top and bottom of this line. A syntactic sphere at the top will be the primary buoyancy element, while an array of glass balls placed just above the acoustic releases will be the backup buoyancy. The site is approximately 240 nautical mi from Woods Hole, Mass. The AMP will return at least ocean temperature, salinity (conductivity) and velocity profile data spanning nearly the full length of the 4,100 m water column. In addition, time series temperature, salinity and velocity data from fixed-depth sensors on the mooring will also be acquired.

Example 2

Figure 2:
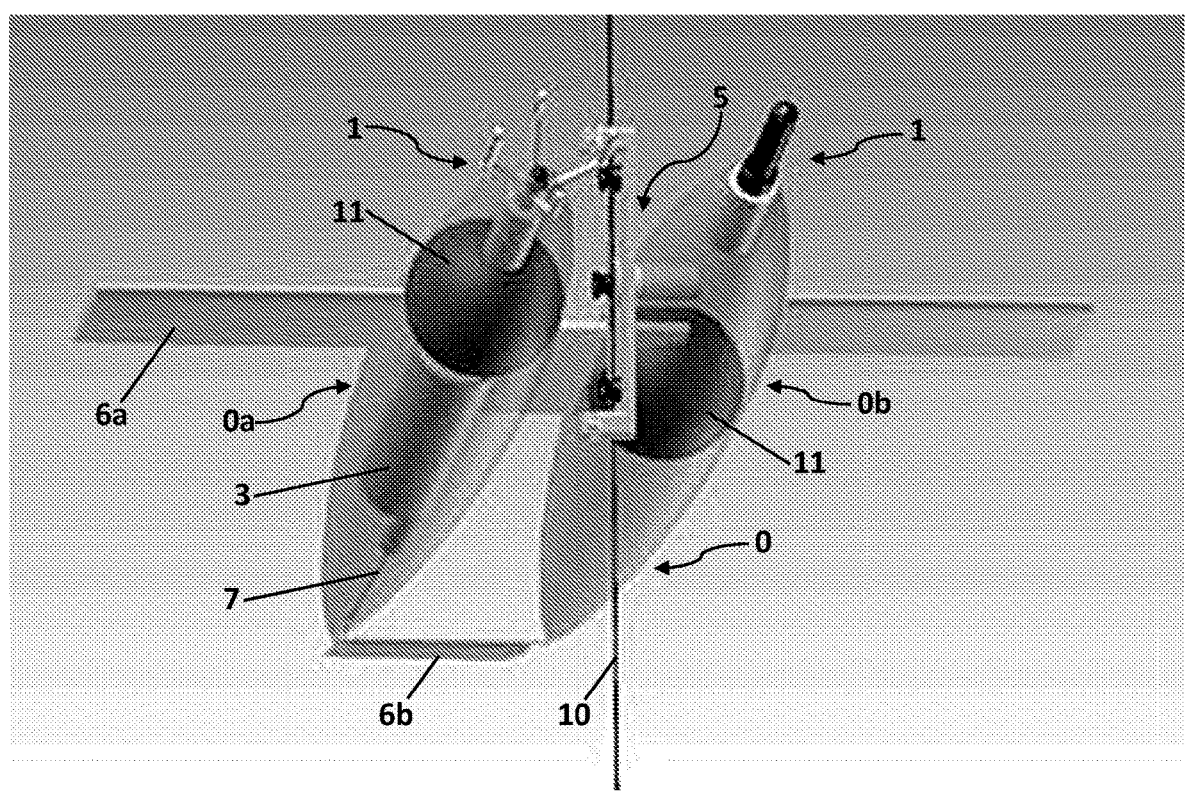
FIG. 2 depicts a rear view of an illustrated embodiment of the present invention disposed on a mooring wire.

As depicted in FIGS. 1 and 2, this embodiment of the inventive device employs two vessel bodies 0a and 0b coupled together spatially separated by a connection near the middle sections of the bodies 0a and 0b. This connection is capable of providing electrical signals, power, data communication, etc. between the two vessel bodies 0a and. 0b or may only provide a mechanical engagement between the two bodies. The mooring cable 10 is typically disposed between the two bodies and engaged with the attachment mechanism 5.

Vessel body 0a is adapted to incorporate the electronics housing 3 and the lift control system 7 within the internal space. As shown, the buoyancy sphere within vessel body 0a is shifted forward relative to buoyancy sphere in vessel body 0b to compensate for the difference in weight distribution. The position of the buoyancy spheres 11 needs to account both for the overall buoyancy/weight and fore-aft balance about the pivoting point of the articulating mechanism 8. Each vessel body may comprise one or more sensors 1 which each retain their sample measurements and data within their respective vessel bodies or more transfer all data to the electronics in the electronics housing 3. Vessel body 0a as shown comprises a sensor such as a MAVS sensor. Vessel body 0b as shown comprises a sensor such as a CTD sensor (e.g., Seabird Electronics 52MP CTD).

Example 3

AMP Specifications

The following table lists specification for one embodiment of the present invention. While the materials listed are suitable, other materials of similar properties may be used. For example, many structural components are comprised of ultra-high molecular weight (UHMW) polyethylene but may be substituted for a material with similar properties including high abrasion resistance, high melt viscosity, low coefficient of friction, chemical resistance, load-bearing strength, and impact strength.

Example 4

This example further describes one embodiment of the AMP device illustrated in FIG. 4. The device comprises a vessel body 0 with an internal hollow space adapted to secure multiple components, particularly mechanical and electrical components, such as electrical housing 3, the sensor array 1, and the drive motor assembly 2. Disposed within the vessel body 0 is the internal frame which in this case is a vertical plate 13 which mounts the electrical housing 3, buoyancy spheres 11 and the lift control system 7 in place. Vertical plate 13 is securely attached within the vessel body 0 and further secured by a tail cone to which part (fin set 6b) of the lift assist system 6 is mounted. A wing set 6a is mounted closer to the leading end of the body 0, operationally coupled with the articulating mechanism 8. Wing set 6a is substantially symmetrical and comprises an angle of attack less than 10 degrees relative to the current flow. Fin set 6b, in this case, comprises four fins wherein the top and bottom fins may be specifically angled by a few degrees (e.g., less than 10 degrees) to compensate for the off-center attachment to the mooring cable 10. Lateral fins of fin set 6b are mechanically engaged with the lift control system 7 which provides an adjustable "elevator" mechanism to set the desired angle of attack and reduces drag on the vessel body 0. The device is attached to a mooring cable 10 wherein the cable passes through the cable guides 5c and retains physical contact with the guide wheels 5b secured on the truck plate 5a.

In its low drag configuration, the device is able to utilize the lift assist system 6 to rapidly climb up and down the cable 10 to complement the propelling force of the drive motor assembly 2 to reliably extend the profiling endurance to about 2 million meters. Additional embodiments of this device may allow the lift assist system 6 to provide 50%, 75%, 90%, 95%, and even up to 100% of the propelling force in presence of strong water currents. The device is adapted to profile in strong currents which are 25 cm/s or great, up to 1 m/s, and up to 2 m/s.

TABLE 1

| | | |
|---|---|---|
| Dimensions | Length | 85.0 in |
| | Width | 17 in |
| Sensor Array | Sensors | CTD Sensor |
| | | MAVS Sensor |
| Drag (at 30 cm/s current) | Total Device Drag | 3.5 N |
| | Vessel Body Drag | 0.2 N |
| Profiling Speed | Up/Down | 25 cm/s-35 cm/s |
| Depth Rating | Typical Use | 6,500 m |
| Materials | Shell | ⅛" Polyethylene |
| | Electronics Housing | Titanium |
| | Vertical Plate | 1" UHMW Polyethylene |
| | Horizontal Plate | 1" UHMW Polyethylene |
| | Truck Plate | 1" UHMW Polyethylene |
| | Idler Arm Support | 1" UHMW Polyethylene |
| | Idler Arm Tab | ¼" UHMW Polyethylene |
| | Drive Engine | Ertalyte ® |
| | Drive Wheel | Ertalyte ® |
| | Fasteners for Tension Spring | Type 316 Stainless Steel |
| Buoyancy | Buoyancy Sphere | 2-12" glass spheres |
| Lift Assist System | Wing Set (2 wings) | NACA 0018 foil profile |
| | | 6 degree angle of attack |
| | | 0.387 $m^2$ wing area |
| | | Lift force 21.3 N |
| | Fin Set (4 fins) | NACA 0012 foil profile |
| | | 6 degree angle of attack |
| Strong Current Use | Current Speed | At least 1 m/s |
| Profiling Endurance | Travel Distance | 2 million meters |

For the purpose of understanding the Articulating Moored Profiler System, references are made in the text to exemplary embodiments of an Articulating Moored Profiler System with various components that may be employed with such a system, only some of which are described herein. It should be understood that no limitations on the scope of the invention are intended by describing these exemplary embodiments. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Furthermore, the described features, advantages, and characteristics may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

Moreover, the terms "substantially" or "approximately" as used herein may be applied to modify any quantitative representation that could permissibly vary without resulting in a change to the basic function to which it is related.

What is claimed:

1. A water profiling device adapted to propel about a cable in an aquatic environment, comprising:
    a vessel body adapted to mount onto an external mooring cable, wherein the vessel body comprises a leading end opposing a tail section;
    a drive system comprising a drive motor assembly;
    an attachment mechanism engaged with the vessel body and the cable;
    an sensor array comprising of one or more sensors adapted to measure a parameter integrated onto or within the vessel body;
    an articulating mechanism, adapted to align the device along the mooring cable relative to a water current flow; and
    a controller in communication with at least one component selected from the group consisting of the attachment mechanism, drive system, the articulating mechanism, and at least one sensor in the sensor array.

2. The device of claim 1, wherein the body is dimensioned to be a hydrodynamically low drag cylindrical body adapted to be oriented along the articulating mechanism relative to the incident three-dimensional relative flow of the current in the aquatic environment.

3. The device of claim 1, wherein the drive system further comprises a drive motor, one or more guide wheels, and one or more drive wheels, wherein the drive system is adapted to maneuver the vessel body vertically along the cable in a forward or reverse direction.

4. The device of claim 1, wherein the sensor array and the drive system are spatially separated.

5. The device of claim 1, wherein at least one sensor of the sensor array is disposed within the body, and the sensor array measures at least one parameter selected from the group consisting of conductivity, temperature, depth, turbidity, dissolved gas, fluorescence, pressure, light level, pH, a chemical, electrical current, battery status, and water current velocity.

6. The device of claim 1, wherein at least one sensor is mounted on the leading end of the device to sample undisturbed water.

7. The device of claim 1, wherein the one or more sensors are controlled by the controller, and each of the one or more sensors is individually selected to operate during a selected measurement cycle or over selected depth ranges.

8. The device of claim 1 further comprising a telemetry means adapted to transmit data obtained by the device to a remote location.

9. The device of claim 1, wherein the articulating mechanism is adapted to pivot vertically and horizontally to align the vessel body relative to the water current flow.

10. The device of claim 1 further comprising a lift assist system comprising one or more of an adjustable wing set, an adjustable fin set, a wing set, a fin set, a tail fin, a lateral fin set, and a combination thereof.

11. The device of claim 10, wherein the articulating mechanism adjusts the orientation of the vessel body such that the ambient current catches at least one component of the lift system thereby extracting lift for propelling the device.

12. The device of claim 10 wherein at least one component of the lift assist system is adapted to be manipulated so as to increase or decrease the force of the current flow impacting the lift system, thereby controlling the lift force generated.

13. The device of claim 12, wherein a wing set are disposed on the lateral sides of the vessel body and wherein the wing set is mechanically coupled to either the drive system or the articulating means so as to allow a rotation of the wing set into or out of the current flow.

14. The device of claim 12, wherein the lift system comprises a wing or fin in the tail section of the vessel body that is adapted to be mechanically manipulated so as to generate or diminish the amount of lift harnessed from the current flow.

15. The device of claim 1, wherein the controller comprises a low power compound processor system adapted to time-stamp and at least temporarily store sensor data.

16. The device of claim 1 further comprising a braking system to decelerate and stop the device on the cable selected from the group consisting of a lock on the drive shaft, a mooring wire clamping mechanism, and a combination thereof.

17. The device of claim 1, wherein the device further comprises two vessel bodies operationally coupled to each other such that they are buoyantly balanced about the cable and attachment mechanism.

18. The device of claim 6, wherein the vessel body pivots along the articulating mechanism into the flow of current such that at least one sensor measures undisturbed water.

19. The device of claim 1, wherein the device is adapted to operate in the presence of strong water current flows by means of the articulating mechanism and operates with a total drag of less than 5 N.

20. A water profiling device adapted to propel about a cable in an aquatic environment, comprising:
    a vessel body adapted to mount onto a cable and accommodate one or more components oriented so as to reduce drag;
    an attachment mechanism, engaged with the vessel body and engaged with the cable adapted with a drive motor assembly that is adapted to propel the device at a selected rate of movement relative to the cable;
    an sensor array, comprised of one or more sensors adapted to measure a parameter;
    an articulating mechanism, adapted to controllably articulate the device about the cable in a horizontal, vertical, or both horizontal and vertical direction to align the device relative to a water current flow and out therefrom;
    a lift assist system adapted to utilize a water current flow to at least partially maneuver the vehicle; and
    a controller;
    wherein the device is adapted to operate in the presence of strong water current flows by means of the articulating mechanism; and the articulating mechanism can further adjust the orientation of the vessel body in at least one of a horizontal and a vertical direction to extract lift for propelling the device.

21. The device of claim 20, wherein at least one sensor of the sensor array is at least partially disposed within the body, and the one or more sensors measures a parameter selected from the group consisting of conductivity, temperature, depth, turbidity, dissolved gas, fluorescence, pressure, light level, pH, a chemical, electrical current, battery status, and water current velocity.

22. The device of claim 20, wherein the body is dimensioned to be a hydrodynamically low drag cylindrical body adapted to self-orient towards the current flow within the aquatic environment.

23. The device of claim 20, wherein the lift assist system comprises at least one component selected from a group consisting of and adjustable wing set, an adjustable fin set, a wing set, a lateral fin, a lateral fin set, and a combination thereof.

24. The device of claim 21, wherein the one or more sensors of the sensor array is disposed within the body, and the one or more sensors measures a parameter selected from the group consisting of conductivity, temperature, depth, turbidity, dissolved gas, fluorescence, pressure, light level, pH, a chemical, electrical current, battery status, and water current velocity.

25. The device of claim 24, wherein one or more sensors is mounted on the leading end of the device to sample undisturbed water when the vessel body is oriented into the current flow by the articulating mechanism.

26. A method of propelling through a water column to measure one or more parameters in an aquatic environment, comprising the steps:
    providing a water profiling device comprising a sensor array of one or more sensors disposed in or on a vessel body;
    mounting said water profiling device on a cable to allow the device to self-orient in relation to the current by means of the articulating mechanism, the cable affixed in the aquatic environment as a mooring cable;
    programming one of more sensors to operate during a selected measurement cycle or over selected depth ranges;
    collecting sensor data from the one or more sensors and at least temporarily storing the sensor data; and
    optionally employing a telemetry means to communicate to a remote location.

27. The method of claim 26, wherein the articulating means adjusts the orientation of the body in at least one of horizontal direction and a vertical direction to extract lift for propelling the device.

28. The method of claim 26 which includes employing a telemetry means in communication with at least one sensor to transmit sensor data and/or sensor programming with a remote location.

29. The method of claim 26, wherein the profiling device employs a lift system comprising at least one component selected from a group consisting of an adjustable wing set, an adjustable fin set, a wing set, a lateral fin, a lateral fin set, and a combination thereof and the lift assist system is adapted to be controllably manipulated to harness the current flow, thereby generating lift that can be used to position the profiling device into a desired position or location.

* * * * *